(12) United States Patent
Kang et al.

(10) Patent No.: US 12,318,306 B2
(45) Date of Patent: Jun. 3, 2025

(54) HEIGHT-ADJUSTABLE SPINAL FUSION CAGE

(71) Applicant: L&K BIOMED CO., LTD., Yongin-si (KR)

(72) Inventors: Gook Jin Kang, Seoul (KR); Youngbo Ahn, Irvine, CA (US)

(73) Assignee: L&K BIOMED CO., LTD., Yongin-si (KR)

( * ) Notice: Subject to any disclaimer, the term of this patent is extended or adjusted under 35 U.S.C. 154(b) by 163 days.

(21) Appl. No.: 17/794,449

(22) PCT Filed: Nov. 5, 2020

(86) PCT No.: PCT/KR2020/015429
§ 371 (c)(1),
(2) Date: Jul. 21, 2022

(87) PCT Pub. No.: WO2021/149899
PCT Pub. Date: Jul. 29, 2021

(65) Prior Publication Data
US 2023/0046487 A1   Feb. 16, 2023

(30) Foreign Application Priority Data
Jan. 23, 2020   (KR) ........................ 10-2020-0009254

(51) Int. Cl.
*A61F 2/44*   (2006.01)
*A61F 2/30*   (2006.01)

(52) U.S. Cl.
CPC .. *A61F 2/4455* (2013.01); *A61F 2002/30316* (2013.01); *A61F 2002/30537* (2013.01)

(58) Field of Classification Search
CPC .......... A61F 2/4455; A61F 2002/30316; A61F 2002/30537
USPC ........................................... 623/17.11–17.16
See application file for complete search history.

(56) References Cited

U.S. PATENT DOCUMENTS

| 2003/0074064 A1 | 4/2003 | Gerbec et al. |
| 2015/0066145 A1 | 3/2015 | Rogers et al. |
| 2017/0224505 A1* | 8/2017 | Butler ...................... A61F 2/44 |
| 2017/0231780 A1 | 8/2017 | D'Urso |
| 2018/0193160 A1 | 7/2018 | Hsu et al. |

OTHER PUBLICATIONS

International Search Report for PCT/KR2020/015429, dated Feb. 23, 2021.

* cited by examiner

Primary Examiner — Eduardo C Robert
Assistant Examiner — Tara Rose E Carter
(74) Attorney, Agent, or Firm — Sughrue Mion, PLLC

(57) ABSTRACT

The present invention relates to a spinal fusion cage which is inserted between vertebral bodies with the lowest height and is height-adjustable in the inserted state, whereby cages having heights within a predetermined range can be replaced by a single cage. Therefore, manufacturers can reduce product groups that need to be produced, and can also reduce product stock. Further, in contrast to the conventional cages having predetermined heights at regular intervals, the height of the inventive cage can be linearly adjusted according to the distance between the vertebral bodies of a patient, and thus a surgery can be performed using the cage adjusted to an optimum height according to the patient's condition.

10 Claims, 10 Drawing Sheets

HEIGHT-ADJUSTABLE SPINAL FUSION CAGE

CROSS REFERENCE TO RELATED APPLICATIONS

This application is a National Stage of International Application No. PCT/KR2020/015429 filed Nov. 5, 2020, claiming priority based on Korean Patent Application No. 10-2020-0009254 filed Jan. 23, 2020, the entire disclosures of which are incorporated herein by reference.

TECHNICAL FIELD

The present invention relates to a height-adjustable spinal fusion cage, and more specifically, to a spinal fusion cage which is inserted between vertebral bodies with the lowest height and is height-adjustable in the inserted state.

BACKGROUND ART

Vertebral bodies, including 32-35 vertebrae and intervertebral discs between vertebrae, form the central part of the body connecting the cranium from the top and the pelvis to the bottom.

Vertebrae consist of seven cervical vertebrae, twelve thoracic vertebrae, five lumbar vertebrae, five sacral vertebrae, and three to five coccygeal vertebrae, from the top, and for adults, five fused sacral vertebrae form the sacrum, and three to five fused coccygeal vertebrae form the coccyx.

For a long time, one of the methods for treating severe spinal diseases has been spinal fusion. Spinal fusion is a surgical procedure to join adjacent vertebral bodies by removing the intervertebral disc and inserting a cage as a substitute.

When such spinal fusion is performed on lumbar vertebrae, the surgical options include posterior lumbar interbody fusion (PLIF), transformational lumbar interbody fusion (TLIF), lateral lumbar interbody fusion (LLIF), oblique lumbar interbody fusion (OLIF), anterior lumbar interbody fusion (ALIF), etc., according to the direction in which a cage is inserted.

Posterior lumbar interbody fusion (PLIF) is a surgical procedure of making an incision along the central line of the spine, opening the site to expose the whole vertebral body, removing part of the back of the vertebrae and removing the disc, and then inserting a PLIF cage.

Posterior lumbar interbody fusion (PLIF), which has been performed for the longest time as a spinal fusion surgical procedure, is needed when performing interbody fusion for two or three joints. However, there is a high possibility that the nerve and ligament are prone to be adhered to the muscle during the procedure, the cutting site is large which requires long recovery time, and some patients suffer from aftereffects following surgery.

A PLIF cage includes a pair of small cages at both sides, and is the smallest implant among those used in spinal fusion surgical procedures.

Transformational lumbar interbody fusion (TLIF) is a surgical procedure of making a small incision along both sides of the spinal muscle to minimally expose the vertebral body, and then inserting a TLIF cage into the disc while removing the facet joints in the direction of the neuropore. During this surgical procedure, there is less bleeding, and the operation time is shortened, which means that it is suitable for a surgery on a single joint. However, for a surgery on various sites, a PLIF surgical procedure is to be performed.

Most TLIF cages having a shape of a circular arc need to be inserted into the vertebral body and rotated such that the convex portion of the TLIF cage is oriented toward the abdomen. The TLIF cage is larger than the PLIF cage in size but has a smaller support area than the LLIF cage or ALIF cage that will be described below.

Anterior lumbar interbody fusion (ALIF) has many advantages such as short recovery time and no concern about adhesion, etc., but has a disadvantage which requires highly advanced techniques because the procedure utilizes an anterior approach from the front (abdominal region) toward spinal bones. The ALIF cage has an advantage of having the largest support area among all the spinal fusion cages.

Lateral lumbar interbody fusion (LLIF) was developed to overcome the disadvantages of ALIF, PLIF and TLIF. LLIF is operated by making an incision in the side of a patient, which more widely expands the distance between the stenosed vertebral bodies, compared to other conventional surgical procedures which make an incision in the back, and also causes little damage on peripheral tissues. However, there is a problem that psoas muscle and peritoneum are on the way of accessing the site, and thus a mistake during the operation may lead to numbness in the thigh, etc. The LLIF cage is smaller than the ALIF cage in size, but smaller than the PLIF cage or TLIF cage.

Oblique lumbar interbody fusion (OLIF) or anterior to psoas fusion (ATP) is a safer and more effective surgical procedure than the LLIF. The OLIF accesses the site from the side in an oblique direction, and has an advantage that the operation can be performed between the fourth lumbar vertebra L4 and the fifth lumbar vertebra L5 where DLIF can hardly be performed because of psoas muscle and peritoneum. Also, the possibility that may damage nerves, which is the problem of LLIF, is significantly low.

Conventional spinal fusion cages are formed of one body with the same cross-sectional area or height using a metal material such as titanium or a polymer material such as PEEK. As such, there are a good number of product groups considering the physique, height, race, gender, etc. of patients. In other words, manufacturers have a burden to manufacture at least tens of product groups to as many as hundreds of product groups by combining three variables, width, length and height.

Also, the distance between vertebral bodies of a patient does not grow at regular intervals. However, when cages are formed of one body, a cage with a proper height should be selected from the existing product groups for operation, which could not meet each patient's condition perfectly.

Many efforts have been made to solve the problem, and a spinal fusion cage capable of adjusting a height has been developed.

U.S. Pat. No. 6,176,882 discloses a height-adjustable cage. The cage of U.S. Pat. No. 6,176,882 comprises walls in a shape of a square box having an open top and an open bottom, an engagement member moving vertically inside the walls, a pair of wedge members pushing out the engagement member, and an adjusting element screw-coupled to the pair of wedge members and adjusting the distance between the pair of wedge members. According to U.S. Pat. No. 6,176,882, the engagement member and the wedge members are simply constrained by the walls of a box shape without being connected with each other, and thus the engagement member shakes.

U.S. Pat. No. 9,034,041, claim 1 of D4, discloses comprising a body assembly, an upper support member 718, and a lower support member 720, wherein the body assembly comprises a first portion 712 and a second portion 714, the first portion 712 and the second portion 714 being movable by a control member along a longitudinal axis. The distance between the upper support member 718 and the lower support member 720 is controlled by a first upper pair of retaining members and a second upper pair of retaining members. As such, U.S. Pat. No. 9,034,041 does not comprise an element for directly guiding the movement of the upper support member 718 and the lower support member 720, and thus the body assembly and the upper support member 718 and the lower support member 720 shake with respect to each other.

PATENT ART LITERATURE

Patent Literature (Patent literature 1) U.S. Pat. No. 6,176,882
(Patent literature 2) U.S. Pat. No. 9,034,041
(Patent literature 3) US2017-02580605A

DETAILED DESCRIPTION OF INVENTION

Technical Task

It is an object of the present invention, which was devised to solve the above problem, to provide a spinal fusion cage which is inserted between vertebral bodies with the lowest height and is height-adjustable in the inserted state.

Means for Solving Technical Task

The present invention, which aims at achieving the above object, relates to a spinal fusion cage, comprising: a first end plate and a second end plate being in contact with adjacent vertebral bodies; a distal moving block fixed to be relatively movable to a plate slope formed at one end of the first end plate and the second end plate; a proximal moving block fixed to be relatively movable to a plate slope formed at the other end of the first end plate and the second end plate; an adjusting member rotatably fixed to the proximal moving block and screw-coupled to the distal moving block, to adjust a distance between the distal moving block and the proximal moving block; a first guide part formed in the first end plate to face the second end plate; and a second guide part formed in the second end plate to face the first end plate, and constraining, by the sliding motion with the first guide part, the motion direction in which the first end plate and the second end plate come close to each other or are separated from each other, wherein the first guide part and the second guide part support the load of the first end plate and the second end plate in the longitudinal direction or width direction, and wherein the first end plate and the second end plate each has a bridge at the end in the distal direction and two legs connected to the bridge extending to the end in the proximal direction.

A block slider is formed in the distal moving block and the proximal moving block, and a plate slider sliding relative to the block slider is formed in the plate slope.

In addition, an auxiliary block slider is arranged around the block slider, and an auxiliary plate slider corresponding to the auxiliary block slider is formed in the first end plate and the second end plate.

In addition, the adjusting member has a screw part screw-coupled to the distal moving block at one end and has a pin space to be rotatably fixed relative to the proximal moving block at the other end, and an adjusting member fin is placed in the pin space through the proximal moving block.

In addition, the first guide part comprises a pillar protruding toward the second end plate, and the second guide part comprises an extension wall protruding toward the first end plate to be slidable relative to the pillar.

In addition, the first guide part has, around the pillar, a receiving part for receiving the extension wall when the first end plate and the second end plate come close to each other.

In addition, the extension wall comprises a first wall and a second wall located in the front and back of the pillar, respectively, along the longitudinal direction of the second end plate, and a third wall connecting the first wall and the second wall to form a groove into which the pillar is inserted.

In addition, a guide groove for guiding insertion of the pillar is formed in the first wall and the second wall.

In addition, an opening communicating with the window is formed between the legs, and part of the proximal moving block is exposed through the opening.

In addition, a recessed groove is formed in a portion exposed through the opening of the proximal moving block.

Effect of Invention

Through the present invention, cages having heights within a predetermined range may be replaced by a single cage. Therefore, manufacturers may reduce product groups that need to be produced, and may also reduce product stock. Further, in contrast to the conventional cages having predetermined heights at regular intervals, the height of the inventive cage may be linearly adjusted according to the distance between the vertebral bodies of a patient, and thus a surgery may be performed using the cage adjusted to an optimum height according to the patient's condition.

Further, as the cage with the lowest height is inserted, the burden to separately manufacture test implants suitable for the distance between the vertebral bodies may be reduced. Also, for doctors, efforts to secure insertion spaces while inserting a plurality of test implants sequentially may be lessened.

BEST MODE FOR CARRYING OUT THE INVENTION

Figure 1:
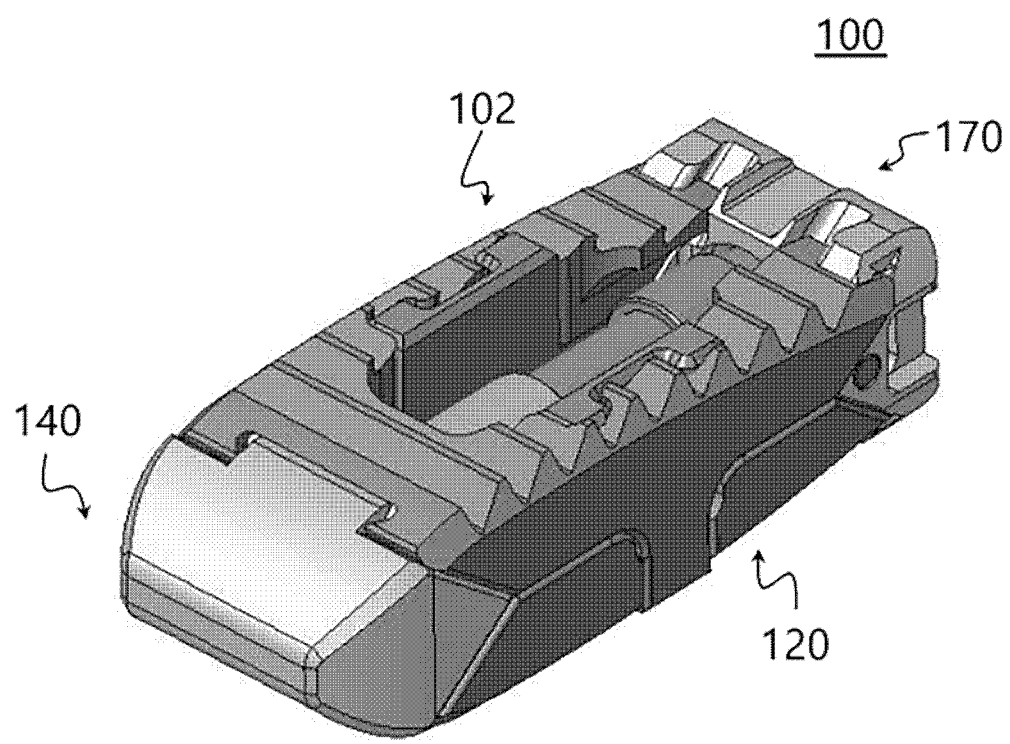
FIG. 1 is a perspective view of embodiment 1 of the spinal fusion cage according to the present invention in the lowest height state.
Figure 2:
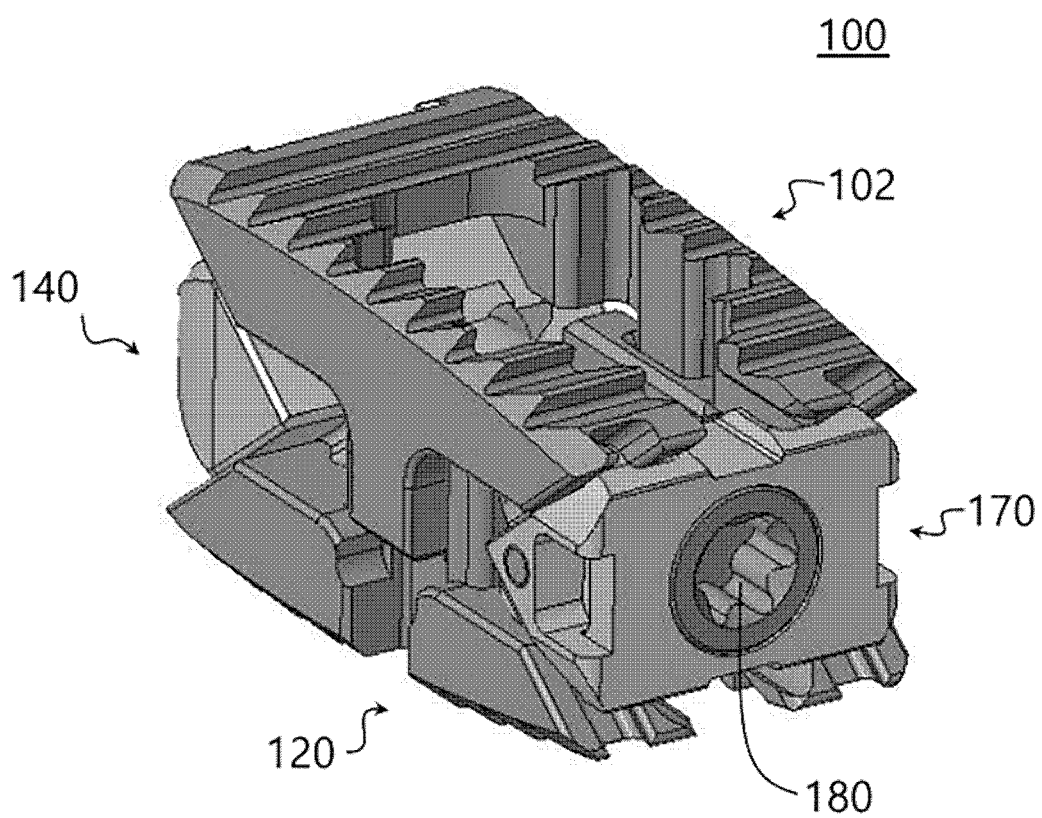
FIG. 2 is a perspective view of the spinal fusion cage of FIG. 1 in the highest height state.
Figure 3:
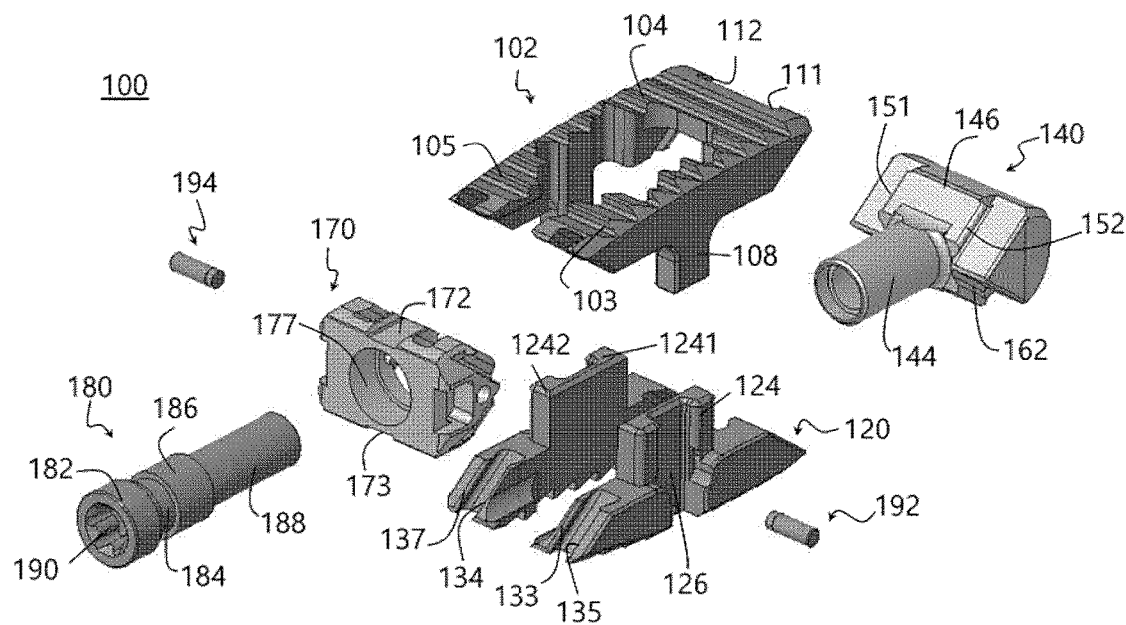
FIG. 3 is an exploded perspective view of the spinal fusion cage of FIG. 1.
Figure 4:
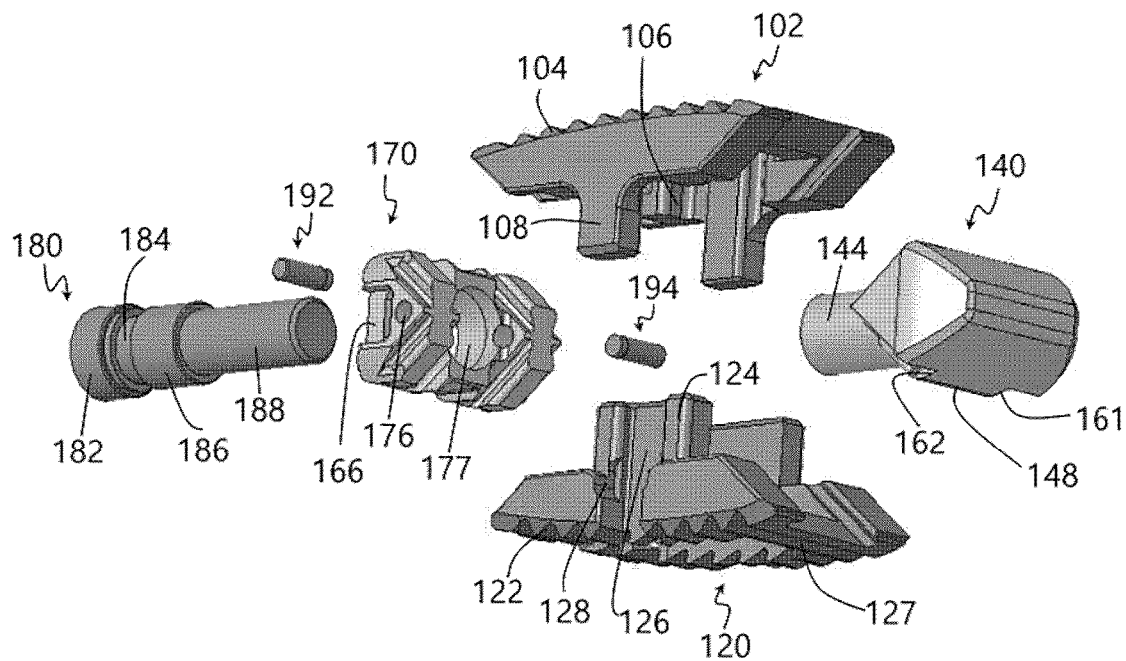
FIG. 4 is an exploded perspective view of the spinal fusion cage of FIG. 1 viewed from another direction, excluding an adjusting member.

Hereinafter, preferred embodiments of the present invention will be explained with reference to the accompanying drawings. In adding reference numerals to the components of the following drawings, the same components are given the same reference numerals as much as possible even if they are displayed on different drawings, and detailed description of known functions and configurations which are determined to unnecessarily obscure the gist of the present invention are omitted.

Hereinafter, the proximal refers to a direction away from insertion, and the distal refers to a direction of insertion.

The spinal fusion cage 100 according to embodiment 1 is described with reference to FIG. 1 to FIG. 13. The spinal fusion cage 100 compirses a first end plate 102 and a second end plate 120 vertically arranged to face each other, a distal moving block 140 and a proximal moving block 170 disposed between the first end plate 102 and the second end plate 120 to move along the distance between the first end plate 102 and the second end plate 120, and an adjusting member 180 passing through the proximal moving block 170 to be connected with the distal moving block 140.

The first end plate 102 and the second end plate 120 have a first plate part 104 and a second plate part 122 which are in contact with vertebral bodies. The first plate part 104 and the second plate part 122 may have tooth-shaped protrusions to prevent separation from the vertebral bodies. In addition, a first window 118 and a second window 138 are formed in the center of the first plate part 104 and the second plate part 122 respectively, into which a bone graft material is inserted.

Figure 5:
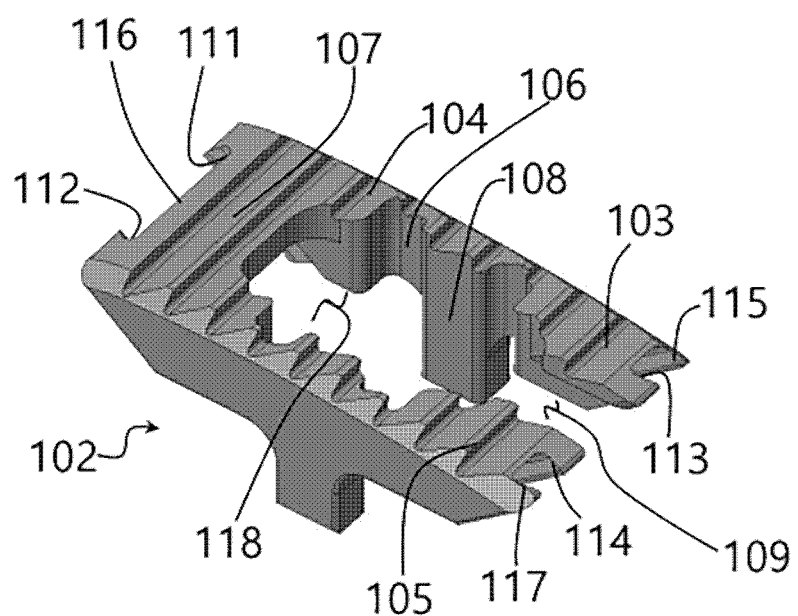
FIG. 5 is a perspective view of the first end plate of FIG. 1.
Figure 6:
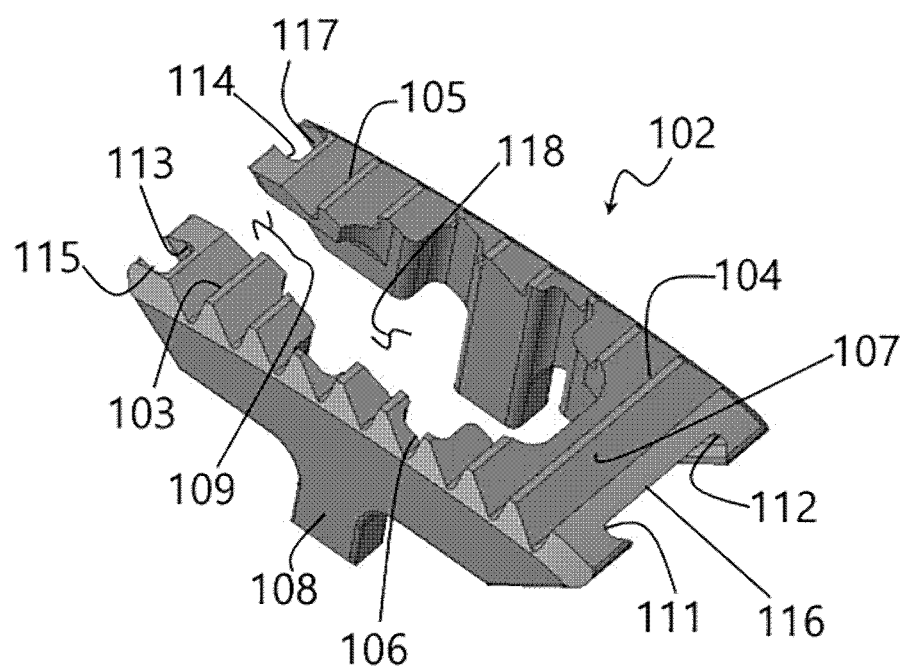
FIG. 6 is a perspective view of the first end plate of FIG. 1 viewed from another direction.

As shown in FIG. 5 and FIG. 6, in the first end plate 102, a first bridge 107 is formed at the end in the distal direction, and two legs 103, 105 connected to the first bridge 107 extend to the end in the proximal direction. The legs 103, 105 are spaced apart from each other to have an approximate U shape with the first bridge 107. Accordingly, a first opening 109 communicating with the first window 118 is formed between the legs 103, 105 in the proximal direction.

Figure 7:
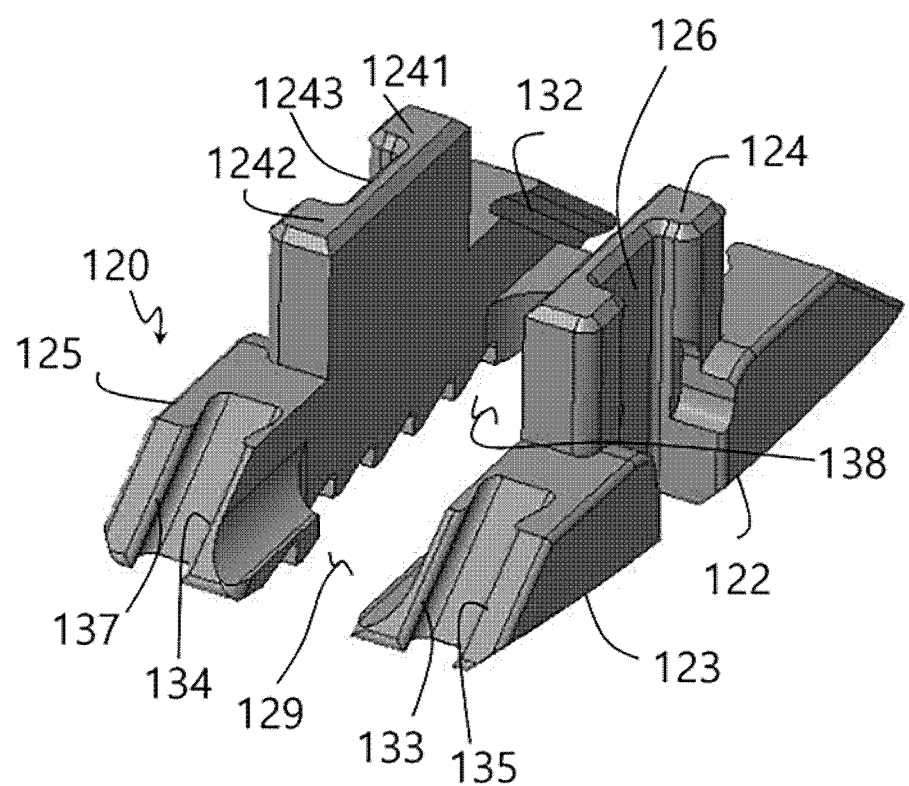
FIG. 7 is a perspective view of the second end plate of FIG. 1.
Figure 8:
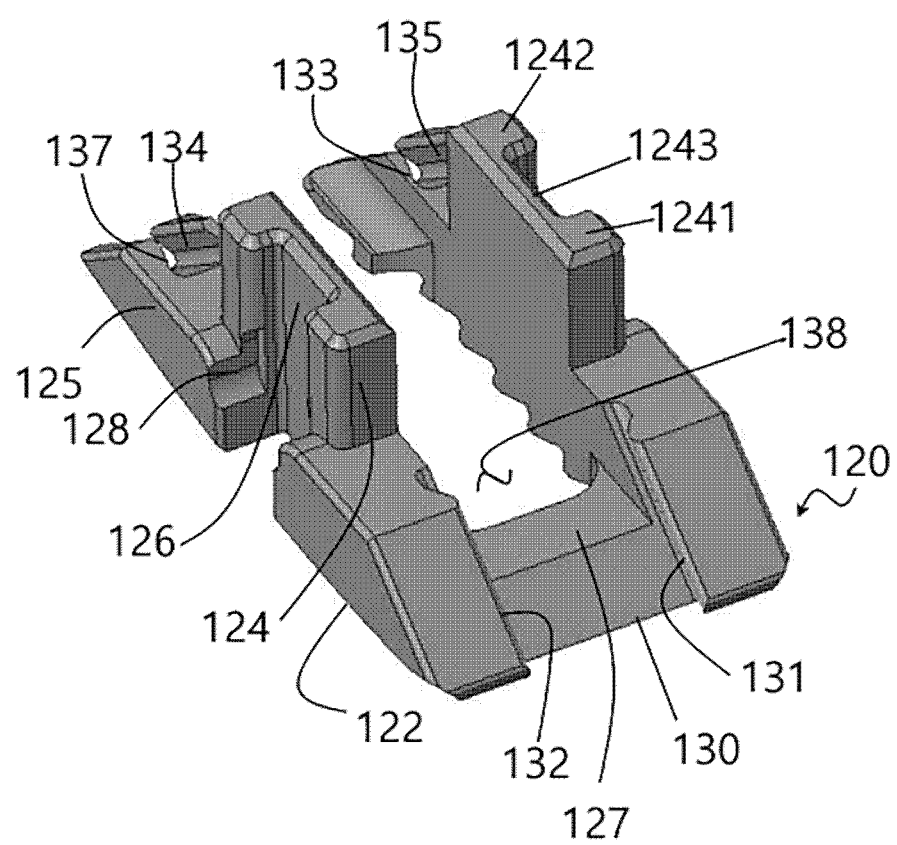
FIG. 8 is a perspective view of the second end plate of FIG. 1 viewed from another direction.

In a similar way, as shown in FIG. 7 and FIG. 8, in the second end plate 120, a second bridge 127 is formed at the end in the distal direction, and two legs 123, 125 connected to the second bridge 127 extend to the end in the proximal direction. The legs 123, 125 are spaced apart from each other to have an approximate U shape with the second bridge 127. Accordingly, a second opening 129 communicating with the second window 138 is formed between the legs 123, 125 in the proximal direction.

The spinal fusion cage 100 has great limits in size and shape because it is inserted into the human body. Also, the spinal fusion cage should have an angle to implement flexibility the spine basically has (an angle in the longitudinal direction of the spine with respect to the transverse plane, i.e., in the sagittal plane direction). Despite the height limit, the adjusting member 180 should have an outer diameter enough to bear the load, and thus the portion of the first end plate 102 or the second end plate 120 on the proximal moving block 170 is to be thinner, which becomes the vulnerable point when the load is applied. Particularly, the greater the angle is, the worse the situation gets. In order to solve the problem, the present invention is characterized by disposing the first opening 109 and the second opening 129 above and below the proximal moving block 170, thereby eliminating the thinner portions in advance.

Figure 9:
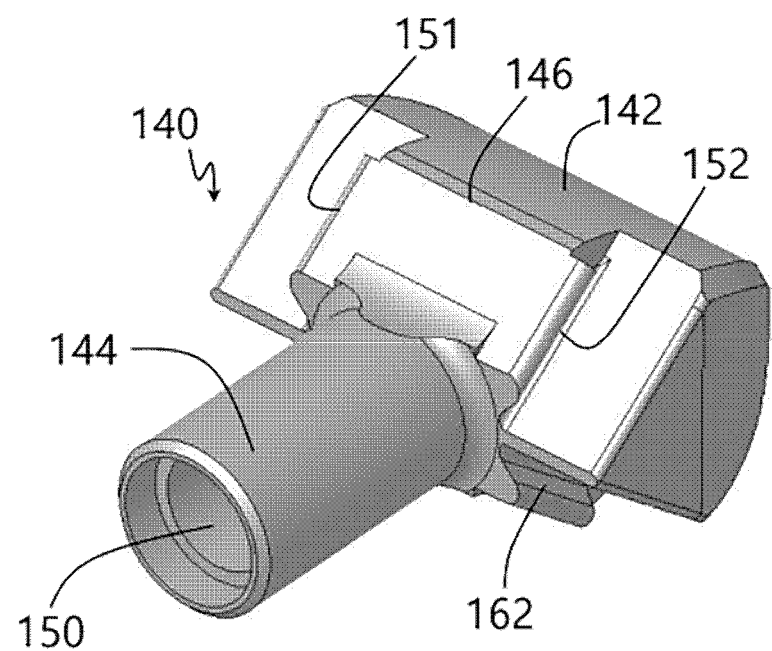
FIG. 9 is a perspective view of the distal moving block of FIG. 1.
Figure 10:
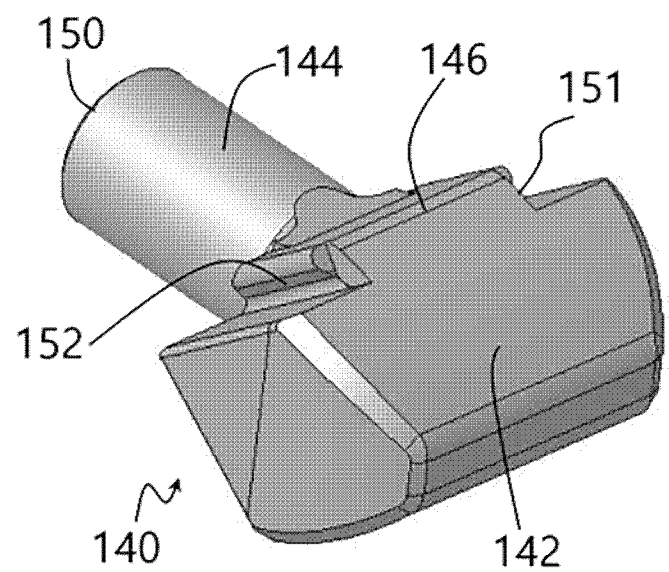
FIG. 10 is a perspective view of the distal moving block of FIG. 1 viewed from another direction.

As shown in FIG. 9 and FIG. 10, a block slider is formed in the distal moving block 140 and the proximal moving block 170, and a plate slider sliding relative to the block slider is formed in the plate slopes of the first and second end plates 102, 120. For the block slider and the plate slider, a rail may be used as described below, and other known means may be used.

A first plate rail 111 and a second plate rail 112 are formed in the distal portion of the first plate part 104, and a third plate rail 113 and a fourth plate rail 114 are formed at the ends of the first and second legs 103, 105 in the proximal portion thereof. The first plate rail 111 and the second plate rail 112 are arranged to face each other, and a first plate groove 116 is formed therebetween. The first plate rail 111, the second plate rail 112, the third plate rail 113 and the fourth plate rail 114 are all inclined to be closer to the center of the first plate part 104 as going from the surface of the first plate part 104 to the thickness direction.

In a similar way, a fifth plate rail 131 and a sixth plate rail 132 are formed in the distal portion of the second plate part 122, and a seventh plate rail 133 and an eighth plate rail 134 are formed at the ends of the third and fourth legs 123, 125 in the proximal portion thereof. The fifth plate rail 131 and the sixth plate rail 132 are arranged to face each other, and a second plate groove 130 is formed therebetween. The fifth plate rail 131, the sixth plate rail 132, the seventh plate rail 133 and the eighth plate rail 134 are all inclined to be closer to the center of the second plate part 122 as going from the surface of the second plate part 122 to the thickness direction.

A first auxiliary plate rail 115 and a second auxiliary plate rail 117 are formed around the third plate rail 113 and the fourth plate rail 114, respectively, at the ends of the first and second legs 103, 105. It is preferable to arrange the first auxiliary plate rail 115 and the second auxiliary plate rail 117 to improve coupling with the proximal moving block 170 because the first and second legs 103, 105 are spaced apart from each other. In embodiment 1, the first auxiliary plate rail 115 and the second auxiliary plate rail 117 are disposed outside the third plate rail 113 and the fourth plate rail 114, respectively, and are arranged to face each other.

A thrid auxiliary plate rail 135 and a fourth auxiliary plate rail 137 are formed around the seventh plate rail 133 and the eighth plate rail 134, respectively, at the ends of the third and fourth legs 123, 125. It is preferable to arrange the third auxiliary plate rail 135 and the fourth auxiliary plate rail 137 to improve coupling with the proximal moving block 170 because the third and fourth legs 123, 125 are spaced apart from each other. In embodiment 1, the third auxiliary plate rail 135 and the fourth auxiliary plate rail 137 are disposed outside the seventh plate rail 133 and the eighth plate rail 134, respectively, and are arranged to face each other.

The distal moving block 140 has a streamlined shape with an insertion part 142 protruding so as to be easily inserted between vertebral bodies in the proximal direction. In addition, the distal moving block 140 has a connection part 144 extending in the distal direction and has a connection screw part 150 having a screw thread inside the connection part 144. In addition, the distal moving block 140 has a first block projection 146 corresponding to the first plate groove 116 of the first end plate 102 and a second block prjection 148 corresponding to the second plate groove 130 of the second end plate 120. A first block rail 151 and a second block rail 152 corresponding to the first plate rail 111 and the second plate rail 112 are formed around the first block projection 146. A fifth block rail 161151 and a sixth block rail 162 corresponding to the fifth plate rail 131 and the sixth plate rail 132 are formed around the third-second block projection 148.

Figure 11:
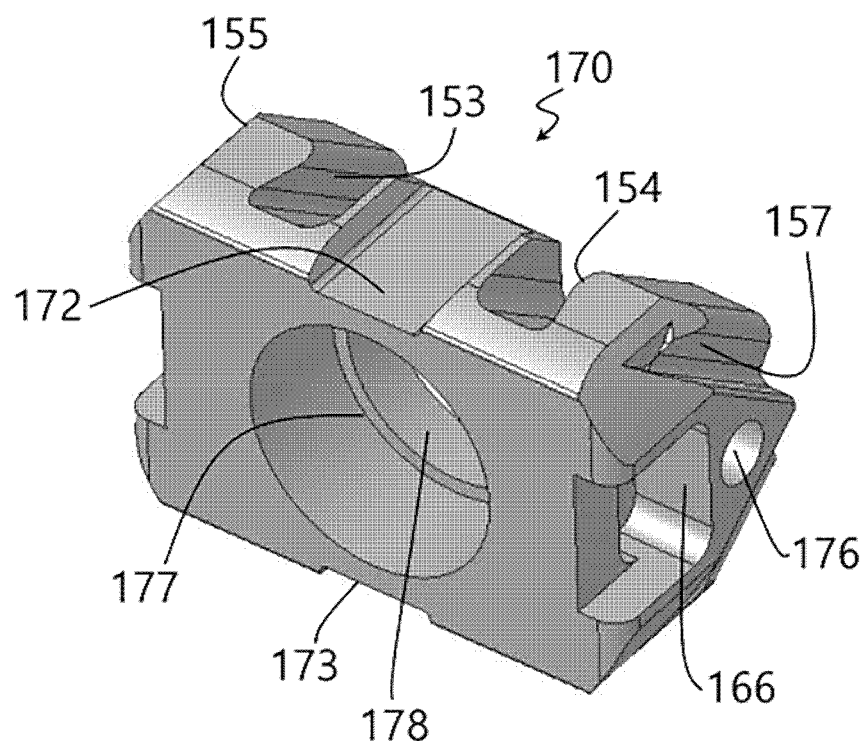
FIG. 11 is a perspective view of the proximal moving block of FIG. 1.
Figure 12:
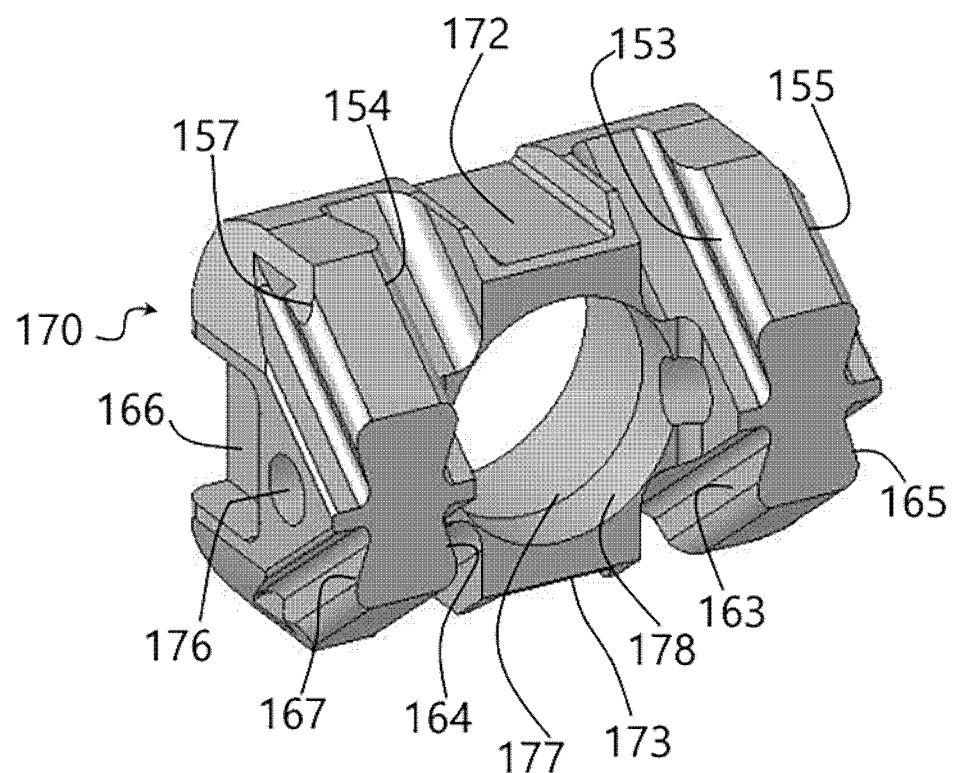
FIG. 12 is a perspective view of the proximal moving block of FIG. 1 viewed from another direction.
Figure 13:
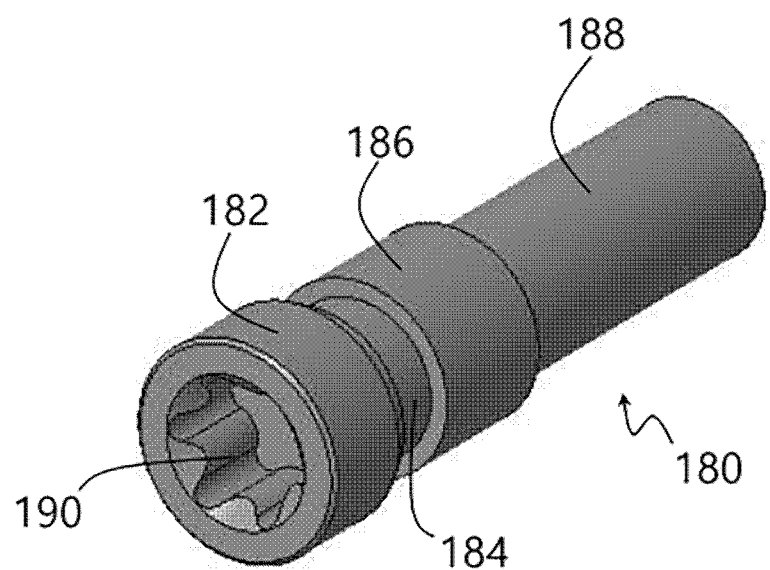
FIG. 13 is a perspective view of the adjusting member of FIG. 1.

As shown in FIG. 11 and FIG. 12, the proximal moving block 170 has a through hole 178 through which part of the adjusting member 180 passes. In the through hole 178, a support jaw 177 for supporting the adjusting member 180 not to be separated in the distal direction may be formed. In addition, in the proximal moving block 170, a first block groove 172 is formed to be exposed to the outside through the first opening 109 of the first end plate 102, and a second block groove 173 is formed to be exposed to the outside through the second opening 129 of the second end plate 120. The first block groove 172 and the second block groove 173 may be used as an auxiliary means when a holder (not shown) holds the spinal fusion cage 100, or may be employed as a pathway for additionally filling a bone graft material after inserting and expanding the spinal fusion cage 100.

A third block rail 153 and a fourth block rail 154 corresponding to the third plate rail 113 and the fourth plate rail 114 are formed around the first block groove 172. A first auxiliary block rail 155 and a second auxiliary block rail 157 corresponding to the first auxiliary plate rail 115 and the second auxiliary plate rail 117 are formed outside the third block rail 153 and the fourth block rail 154, respectively.

Then, a seventh block rail 163 and an eighth block rail 164 corresponding to the seventh plate rail 133 and the eighth plate rail 134 are formed around the second block groove 173. A third auxiliary block rail 165 and a fourth auxiliary block rail 167 corresponding to the third auxiliary plate rail 135 and the fourth auxiliary plate rail 137 are formed outside the seventh block rail 163 and the eighth block rail 164, respectively.

Then, a fixing pinhole 176 for accommodating a first and a second fixing pin 192, 194 is formed at both sides of the proximal moving block 170. In addition, a fastening part 166 is formed at both sides of the proximal moving block 170 to hold the spinal fusion cage 100 by a device (not shown).

The distal moving block 140 and the proximal moving block 170 have an approximate wedge shape and lift or lower the first end plate 102 and the second end plate 120.

The adjusting member 180 may have an approximate bolt shape. In other words, the adjusting member 180 has a head 182 and an adjusting screw part 188. The head 182 is located in the opening formed in the proximal direction of the through hole 178, and the adjusting screw part 188 passes through the through hole 178 and is screw-coupled to the connection screw part 150 of the connection part 144. A tool space 190 connectable to a tool that is not shown is formed in the head 182. A support part 186 is positioned between the head 182 and the through hole 178 to support rotation while being in contact with the inner wall of the through hole 178. In addition, a pin space 184 is formed around the support part 186 to accommodate the ends of the fixing pins 192, 194 inserted through the pinholes 176 of the proximal moving block 170. As a result, the adjusting member 180 is rotatable in position.

A pair of pillars 108 is formed at both sides of the first plate part 104, the first plate leg 103 and the second plate leg 105, in the thickness direction, i.e., in the direction toward the second end plate 120. A receiving part 106 for receiving an extension wall 124 that will be described below is formed around the pillar 108. An extension wall 124 is formed at both sides of the second end plate 120, the third plate leg 123 and the fourth plate leg 125, in the thickness direction, i.e., in the direction toward the first end plate 102, and a groove 126 for receiving and guiding the pillar 108 is formed inside the extension wall 124. As a result, the motion of the first end plate 102 and the second end plate 120 to come close to each other or be separated from each other is constrained by which the pillar 108 moves vertically while being received in the groove 126.

In addition, the extension wall 124 comprises a first wall 1241 and a second wall 1242 located in the front and back of the pillar 108, respectively, along the longitudinal direction of the second end plate 120, and a third wall 1243 connecting the first wall 1241 and the second wall 1242 to form the groove 126 into which the pillar 108 is inserted. In other words, the extension wall 124 has an approximate U shape when viewed from the top and encloses the pillar 108.

The first wall 1241 and the second wall 1242 have a thickness smaller than a value obtained by subtracting the length in the width direction of the second window 138 from the length in the width direction of the second plate part 122. This is because the first wall 1241 and the second wall 1242 are inserted into the receiving part 106 of the first end plate 102. Also, it is possible that the pillar 108 has a thickness in the width direction ¼ greater than and ½ smaller than a value obtained by subtracting the length in the width direction of the first window 118 from the length in the width direction of the first plate part 104. This is because the thickness becomes greater as much as the depth of the groove 126 into which the pillar 108 is inserted.

In addition, a guide groove 128 for guiding insertion of the pillar 108 into the groove 126 may be formed in the first wall 1241 and the second wall 1242, because the thickness of the pillar 108 is greater than the thickness of the first wall 1241 and the second wall 1242.

The spinal fusion cage 100 is constructed as described above, a tool such as screwdriver, etc., is inserted into the tool space 190 and rotated in one direction, and thereby the proximal moving block 170 and the distal moving block 140 come close to each other. As a result, the motion is possible such that the first end plate 102 and the second end plate 120 are separated from each other. In a similar way, the tool is inserted and rotated in the other direction, and thereby the proximal moving block 170 and the distal moving block 140 are distanced apart from each other. As a result, the motion is possible such that the first end plate 102 and the second end plate 120 come close to each other.

As described above, the present invention has been explained with reference to preferred embodiments of the present invention, but it may be understood that those skilled in the art can variously modify and change the present invention within the scope without departing from the spirit and scope of the present invention as described in the claims below.

INDUSTRIAL APPLICABILITY

The present invention can respond to heights in a predetermined range using a single cage, thereby lessening the burden of stock and production, and reducing repetitive works during surgery which not only reduces doctor's efforts, but also shortens operation time thereby decreasing bleeding volume and significantly shortening the patient's recovery time. Therefore, it is expected to be widely used in the relevant field.

DESCRIPTION REFERENCE NUMERALS

100: spinal fusion cage
102: first end plate
103: first plate leg
104: first plate part
105: second plate leg
106: receiving part
107: first bridge
108: pillar
109: first opening
111: first plate rail
112: second plate rail
113: third plate rail
114: fourth plate rail
115: first auxiliary plate rail
116: first plate groove
117: second auxiliary plate rail
118: first window
120: second end plate
122: second plate part
123: third plate leg
124: extension wall
125: fourth plate leg
126: groove
127: second bridge
128: guide groove
129: second opening
130: second plate groove
131: fifth plate rail
132: sixth plate rail
133: seventh plate rail
134: eighth plate rail
135: third auxiliary plate rail
137: fourth auxiliary plate rail
138: second window
140: distal moving block
142: insertion part
144: connection part
146 first block projection
148: second block projection
150: connection screw part
151: first block rail
152: second block rail
153: third block rail
154: fourth block rail
155: first auxiliary block rail
157: second auxiliary block rail
161: fifth block rail
162: sixth block rail
163: seventh block rail
164: eighth block rail
165: third auxiliary block rail
166: fastening part
167: fourth auxiliary block rail
170: proximal moving block
172: first block groove
173: second block groove
176: pinhole
177: support jaw
178: through hole
180: adjusting member
182: head
184: pin space
186: support part
188: adjusting screw part
190: tool space
192, 194: fixing pin
1241: first wall
1242: second wall
1243: third wall

What is claimed is:

1. A spinal fusion cage, comprising:
a first end plate and a second end plate being in contact with adjacent vertebral bodies;
first plate slopes located at one end of each of the first end plate and the second end plate;
a distal moving block fixed to be relatively movable to the first plate slopes;
second plate slopes formed at other end of each of the first end plate and the second end plate;
a proximal moving block fixed to be relatively movable to the second plate slopes;
an adjusting member rotatably fixed to the proximal moving block and screw-coupled to the distal moving block, to adjust a distance between the distal moving block and the proximal moving block;
a first guide part formed in the first end plate to face the second end plate; and
a second guide part formed in the second end plate to face the first end plate, and constraining, by the sliding motion with the first guide part, the motion direction in which the first end plate and the second end plate come close to each other or are separated from each other,
wherein the first guide part and the second guide part support the load of the first end plate and the second end plate in the longitudinal direction or width direction, and
wherein the first end plate and the second end plate each has a bridge at the one end in the distal direction and two legs connected to the bridge extending to the other end in the proximal direction,
wherein a first window is formed in the center of the first end plate, into which a bone graft material is inserted, and
wherein a second window is formed in the center of the second end plate, into which a bone graft material is inserted.

2. The spinal fusion cage of claim 1, wherein block sliders are formed in each of the distal moving block and the proximal moving block, and a plate sliders sliding relative to the block sliders are formed in each of the first plate slopes and the second plate slopes.

3. The spinal fusion cage of claim 2, wherein auxiliary block sliders are arranged around the block sliders, and an auxiliary plate slider corresponding to the auxiliary block sliders are formed in each of the first end plate and the second end plate.

4. The spinal fusion cage of claim 1, wherein the adjusting member has a screw part screw-coupled to the distal moving block at one end and has a pin space to be rotatably fixed relative to the proximal moving block at the other end, and an adjusting member pin is placed in the pin space through the proximal moving block.

5. The spinal fusion cage of claim 1, wherein the first guide part comprises a pillar protruding toward the second end plate, and the second guide part comprises an extension wall protruding toward the first end plate to be slidable relative to the pillar.

6. The spinal fusion cage of claim 5, wherein the first guide part has, around the pillar, a receiving part for receiving the extension wall when the first end plate and the second end plate come close to each other.

7. The spinal fusion cage of claim 6, wherein the extension wall comprises a first wall and a second wall located in the front and back of the pillar, respectively, along the longitudinal direction of the second end plate, and a third wall connecting the first wall and the second wall to form a groove into which the pillar is inserted.

8. The spinal fusion cage of claim 7, wherein a guide groove for guiding insertion of the pillar is formed in the first wall and the second wall.

9. The spinal fusion cage of claim 1, wherein a first opening communicating with the first window is formed between the legs at the other end of the first end plate,
   wherein a second opening communicating with the second window is formed between the legs at the other end of the second end plate,
   wherein part of the proximal moving block is exposed through the first and second openings.

10. The spinal fusion cage of claim 9, wherein first and second block grooves are formed in the proximal moving block, wherein the first block groove is exposed to the outside through the first opening, and the second block groove is exposed to the outside through the second opening.

* * * * *